United States Patent
O'Mahony

(10) Patent No.: US 7,615,028 B2
(45) Date of Patent: Nov. 10, 2009

(54) EXTRACORPOREAL BLOOD TREATMENT AND SYSTEM HAVING REVERSIBLE BLOOD PUMPS

(75) Inventor: John J. O'Mahony, Galway (IE)

(73) Assignee: CHF Solutions Inc., Brooklyn Park, MN (US)

( * ) Notice: Subject to any disclaimer, the term of this patent is extended or adjusted under 35 U.S.C. 154(b) by 370 days.

(21) Appl. No.: 11/002,442

(22) Filed: Dec. 3, 2004

(65) Prior Publication Data
US 2006/0122552 A1 Jun. 8, 2006

(51) Int. Cl.
*A61M 37/00* (2006.01)
(52) U.S. Cl. ............... 604/5.01; 604/4.01; 604/6.05; 604/6.06; 604/6.09; 604/6.11; 422/44; 422/45; 422/46; 422/47; 422/48; 210/645; 210/646; 210/647; 210/648; 210/649; 210/650; 210/651; 210/652
(58) Field of Classification Search ............... 604/5.01, 604/4.01, 6.05, 6.06, 6.09, 6.11; 422/44–48; 210/645–652
See application file for complete search history.

(56) References Cited

U.S. PATENT DOCUMENTS

| | | | | |
|---|---|---|---|---|
| 4,828,543 | A * | 5/1989 | Weiss et al. | 604/6.09 |
| 5,114,580 | A * | 5/1992 | Ahmad et al. | 210/646 |
| 5,120,303 | A * | 6/1992 | Hombrouckx | 604/6.05 |
| 5,662,806 | A | 9/1997 | Keshaviah et al. | |
| 5,690,831 | A | 11/1997 | Kenley et al. | |
| 5,725,775 | A | 3/1998 | Bene et al. | |
| 5,808,181 | A | 9/1998 | Wamsiedler et al. | |
| 5,894,011 | A * | 4/1999 | Prosl et al. | 422/44 |
| 5,947,911 | A | 9/1999 | Wong et al. | |
| 6,090,048 | A | 7/2000 | Hertz et al. | |
| 6,585,675 | B1 * | 7/2003 | O'Mahony et al. | 604/4.01 |
| 6,743,193 | B2 * | 6/2004 | Brugger et al. | 604/6.1 |
| 7,087,033 | B2 * | 8/2006 | Brugger et al. | 604/4.01 |
| 7,147,613 | B2 * | 12/2006 | Burbank et al. | 604/5.01 |
| 2004/0044302 | A1 * | 3/2004 | Bernard et al. | 604/6.09 |

FOREIGN PATENT DOCUMENTS

WO WO 03/006944 A2 1/2003

OTHER PUBLICATIONS

PCT/US01/42861 International Search Report.
PCT/US01/42861 Written Opinion.
PCT/US01/42861 International Preliminary Examination Report.
European Search Report dated Jun. 12, 2006.

* cited by examiner

*Primary Examiner*—Tatyana Zalukaeva
*Assistant Examiner*—Ginger T Chapman
(74) *Attorney, Agent, or Firm*—Nixon & Vanderhye P.C.

(57) ABSTRACT

An extracorporeal blood treatment system including: a blood circuit having a first blood passage coupled at a first end to a first end of a blood treatment device and a second blood passage coupled at a first end to a second end of the treatment device, wherein the first and second blood passages each have a second end adapted to be coupled to a vascular system of a human patient; a first blood pump connectable to the first blood passage and a second blood pump connectable to the second blood passage, wherein said first and second blood pumps are adapted to move blood through the first and second blood passages in a first direction and in a reverse direction, and a pump controller operatively connected to the first and second blood pumps, said controller operates the blood pumps to cyclically move blood through the first and second blood passages in the first direction and the reverse direction.

12 Claims, 8 Drawing Sheets

800

EXTRACORPOREAL BLOOD TREATMENT AND SYSTEM HAVING REVERSIBLE BLOOD PUMPS

FIELD OF INVENTION

The present invention relates to the field of extracorporeal blood treatment systems. In particular, the invention relates to reversible peristalic pumps for a portable extracorporeal treatment device.

BACKGROUND OF THE INVENTION

Congestive Heart Failure (CHF) is a form of heart disease still increasing in frequency. According to the American Heart Association, CHF is the "Disease of the Next Millennium". The number of patients with CHF is expected to grow even more significantly as an increasing number of the "Baby Boomers" reach 50 years of age.

CHF is a condition that occurs when the heart becomes damaged and reduces blood flow to the organs of the body. If blood flow decreases sufficiently, kidney function becomes impaired and results in fluid retention, abnormal hormone secretions and increased constriction of blood vessels. These results increase the workload of the heart and further decrease the heart's pumping ability and, in turn, causes further reductions in blood flow to the kidney. It is believed that the progressively-decreasing perfusion of the kidney is a principal non-cardiac cause perpetuating the downward spiral of the "Vicious Cycle of CHF". Moreover, the fluid overload and associated clinical symptoms resulting from these physiologic changes are a predominant cause for excessive hospital admissions, poor quality of life and large costs to the health care system due to CHF.

There is a long-felt demand for a miniature and portable extracorporeal fluid treatment devices for patients suffering from repeated fluid overload. Such a device might be worn during the day as the patient moves about. The device would preferably be easy to use. If the procedure for inserting catheters percutaneously is too complicated, it will be difficult to have sufficiently trained clinical personnel available to insert the catheter. Standard OTN (Over The Needle) catheters generally require nurses with intravenous (IV) insertion experience to insert catheters to gain blood access for the fluid removal device. When midline catheters are used for accessing blood peripherally, the insertion of the catheter is limited to clinicians with the required training. To insert PICC (Peripherally Inserted Central Catheter) line requires IV nurses with training in seldinger insertion technique and doctors with similar training.

Utilizing an ultrafiltration fluid removal device that uses standard IV access would greatly simplify the process. A simpler approach would be to use an implanted port whereby the nurse could quickly gain access to blood flow. Implanted ports are commonly used for drug infusion therapies and are ideal for long term access. Implanted ports are also accessed via IV needles. Ports have reduced infection rates when compared with standard central venous percutaneous catheters and are ideal for repeatable access over long periods of time.

Peripheral IV blood access is not without its own inherent issues, which include: (1) The blood flow may be limited and intermittent with peripheral access because the further down the peripheral vein tree blood flow is accessed there is less blood flow is available and the more that the available blood flow is subject to fluctuations in flow. Implanted ports can overcome many of these limitations because they are placed centrally. (2) The majority of nurses are comfortable using OTNs with sizes of 20 G and less. These are simpler to insert, cause less trauma and facilitate multiple insertions. If larger catheters gauge sizes are required, the percentage of nurses that can gain access without trouble quickly diminishes which would cause a further hurdle to the usage of such an ultrafiltration device. However, the smaller the gauge size of the catheter the smaller its internal diameter which results in a limitation in the maximum blood flow that can be achieved. This limitation is due to the maximum positive and negative pressures that blood can safely be exposed to without compromising patient safety. Patients with fluid overload also suffer from peripheral edema and the edema tends to hide the veins by placing them further from the skin surface making it more difficult to locate them. In these cases the clinician resorts to multiple sticks before a vein is located. The smaller the IV catheter the more acceptable such a procedure is. Larger gauge needles increase the trauma to the arm and are less acceptable to patients. Implanted ports will overcome many of these limitations because access is gained via a septum which when located makes gain blood flow access relatively simple.

When low blood flow is used in an extracorporeal device, it creates a significant engineering challenge. In general the lower the blood flow, the longer the residence time of blood extracorporeally and the greater the propensity of the device to clot. Lower blood flows increases the difficulty of pressure sensors to reliably detect infusion disconnects. Lower blood flows yield lower pressure drops that result in a large pressure sensor signal to noise ratio between the pressure drop attributed to the access and variations in pressure due to patient movement. When peripheral vein access is used or when a patient is treated for an extended period of time, it is normal to expect the patient to be mobile and that the patient will move about, bend over and lift their arms to stretch occasionally during treatment. Every centimeter (cm) in height change of the patient's arm having the withdrawal and/or infusion catheter results in a 0.75 mmHg pressure increase or decrease in the blood circuit due to the resultant change in static head pressure. Accordingly, the ratio between variation in static head pressure due to patient movement and needle pressure drop due to blood flow should be relatively insignificant so that false alarms will not be annunciated. Disconnection of blood tubes/access in the circuit are generally detected by a reduction in the pressure drop across a needle. It may be hard to distinguish pressure fluctuations due to patient motion and to needle disconnects. It is accepted medically that a blood loss of 100 ml or less will not result in the patients' health being compromised. In the case of the typical dialysis machine this time period is 100 ml/400 ml/min or 15 seconds. Disconnection algorithms have to be extremely sensitive to ensure patient safety. In hemodialysis standards, such as IEC 60601-2-16, the standards committee was aware that there are inherent limitations in using pressure measurements for detecting disconnects which is why devices which use high blood flows have been limited to ICU and dialysis clinic use up until recently. It is also recognized as being an increased risk for the use of home dialysis.

SUMMARY OF INVENTION

A novel extracorporeal blood treatment system is proposed that takes advantage of the low blood flow while achieving a medically significant volume of ultrafiltrate removal and device portability.

It is medically accepted that a blood loss of 100 ml or less will not result in the patients' health being compromised. In the USA, MDR (Medical Device Report) are typically filled out if a blood loss of over 100 ml occurs. In the performance dialysis a blood loss of more than 100 ml may occur in less than 15 seconds. Thus disconnection algorithms have to be extremely sensitive and quick for blood circuits having high volume blood flow, such as in dialysis machine.

With high blood flow, disconnects of blood lines in extracorporeal devices must be detected as soon as possible. Without quick detection of disconnections, the patient could bleed to death in a relatively short period of time. A lower blood flow device allows for a longer detection time while maintaining safety before blood loss becomes detrimental to the patient. The lower the blood flow the longer the time which may be allowed to determine that a blood loss is occurring.

The blood circuit may be symmetrical which facilitates ultrafiltration when the blood pumps are rotating clockwise or counterclockwise. A first blood pump withdraws blood into a withdrawal tube of the blood circuit. A second blood pump draws blood from a filter and infuses the blood into the vascular system of the patient. A third pump draws filtrate from the filter and controls the rate of filtrate flow to a filtrate collection bag. The withdrawal and infusion tubes of the circuits may be connected to an implanted blood port(s) under the skin of the patient or peripheral IV needles inserted into peripheral veins.

In one embodiment, a portable ultrafiltration system is proposed that is capable of removing at least 1 liter of filtrate fluid every 24 hrs, and operating on battery for at least 8 hrs. The disposable circuit component of the system is inexpensive and robust so as to undergo the challenges of ambulatory care. The circuit may be able to operate for 24 hrs. or more before replacement with a new circuit. A pump controller of the system regulates the flow rate of blood through the circuit. The blood flow may be set by the controller in a range of 5 to 15 ml/min. The controller may adjust the maximum blood flow setting in, for example, increments of 1 ml/min based upon the physiological blood flow present.

The withdrawal and infusion tubes of the circuit both pass through an air detector(s) before connection to the patient. The air detector sense air bubbles in the blood tubes to detect disconnections in the blood tube. Disconnection occurring downstream of the air detectors are not sensed by the air detectors until the blood flow is reversed. When the pumps reversed the blood flow, air drawn in through the disconnection or leak is sensed as the air bubbles flow past the air detector. Reversal of the blood flow ensures that disconnections and leaks in the blood circuit are sensed by the air detectors.

The blood flow is reversed at a cyclical rate to prevent a large volume of blood from being discharged from a leak or disconnection. The reversal cycle period is determined by the pump controller as a function of the set blood flow rates. Reversals are set to occur frequently or periodically such that blood loss due to disconnect never exceeds 100 ml. For example, when the blood flow is set to 5 ml/min the blood pump is reversed in direction every 20 minutes. During a first twenty minute period of operation both blood pumps are rotate clockwise. At the end of the first period, the pumps both reverse to rotate counterclockwise and thereby reverse the flow direction of blood through the circuit. At the end of the second twenty minute period, the cycle repeats. If a disconnect were to occur during operation, at 5 ml/min and a 20 minute cycle, a maximum of 100 ml is withdrawn from the patient and potentially lost.

Alternatively, if the blood flow is set to 15 ml/min the period in time between pump reversals is reduced to 6.66 minutes because 15 ml/min×6.66 min=100 ml. Reversal times for flow rates between 5 and 15 ml/min can be calculated from the simple equation: Reversal time (min)=100 (ml)/flow rate (ml/min). A safety factor, or allowance, could be subtracted from the reversal time to account for possible blood loss through the access sites due to venous pressure.

Reversing the blood flow ensures that the occurrence of a circuit disconnection is detected within two periods of the pump rotation cycle. If a disconnection or leak were present in the circuit, air would be entrained in the blood tube. The ultrafiltration device detects the presence of the leak in either the clockwise or anticlockwise cycle blood withdrawal cycle. Blood loss will not exceed 100 ml or other such preset volume because the presence of a leak will be detected as soon as the leak is under negative pressure and air is entrained and pumped past the air detector. The circuit blood volume is less than 5 ml. This low volume ensures the blood is outside the body a minimal amount of time and reduces the chances of blood clotting within the circuit. The circuit blood volume includes any possible extensions and access devices.

The periodic reversals of the blood pumps have a number of other advantages including: the reversals of the blood flow reduces the polarization layer of protein deposited upon the filter membrane (much like the static charge on a comb can be reduced by reversing the direction that the comb is being rubbed); and proteins and white blood cells which aggregate in the header of the filter which do not pass through the filter are returned to the patient before they result in the formation of a clot.

Once a reversal in blood pump direction is initiated, the removal of filtrate from the filter is temporarily stopped for the duration of time it takes for the blood in the filter and circuit to pass back through the filter. Stopping the filtrate pump during this period avoids filtering the blood twice. Double filtration of the same volume of blood would increase the propensity of the filter to clot. The ultrafiltration cessation time is a function of the volume of blood between the filter and the patient. For example, if the blood volume between the filter and patient is 1 ml in the infusion line and the blood flow rate is 5 ml/min, the ultrafiltration cessation period should be 12 seconds (1 ml/5 ml/min) or greater. It may also be necessary to clear the volume of blood in the blood access device, e.g. implanted port, before resuming filtration. If the access being used is an implanted port with a blood volume of 3 ml then it will be beneficial to allow this volume of blood to also be displaced back into the blood stream before reinitiating ultrafiltration.

Three pumps have a number of advantages including: it is possible to keep the pressure in the filter positive or negative at all times by controlling the rate of the two blood pumps with respect to the rate of ultrafiltration which has the advantage of obviating the need for measuring negative pressure or for detecting the presence of a leak; reducincing significant pressure delays between the withdrawal pressure being sensed and the withdrawal catheter and the infusion pressure being sensed and the infusion catheter which has the advantage of less damping and signal delays of the pressure being measured facilitating a higher bandwidth control; simultaneously controlling withdrawal, infusion and filter pressures; and it is no longer necessary to use a weight scale for the filtrate collection bag because filter pressures will become excessively high or low if the difference between the two blood pump flow rates do not closely match the ultrafiltrate pump flow rate. Thus it is possible to continuously reference and check the flow of each pump against each other.

One of the engineering challenges in developing a portable system is to limit the power requirements of the device which in turn will minimize the weight of the battery and the size of the overall device. This portable system uses novel power management systems in conjunction with highly efficient motors to minimize the power consumption to less than 10 watts. This enables portable therapy operation for up to 12 hours with a battery weight of less than 1.5 lb battery. Such an implementation makes it feasible to produce a very reliable low flow portable ultrafiltration device minimizing the costs of the disposable device by simplifying its design while mitigating all known hazards in a safe and effective manner.

The invention may be embodied as an extracorporeal blood treatment system comprising: a blood circuit comprising a first blood passage coupled at a first end to a first end of a blood treatment device and a second blood passage coupled at a first end to a second end of the treatment device, wherein said first and second blood passages each have a second end adapted to be coupled to a vascular system of a human patient; a first blood pump connectable to the first blood passage and a second blood pump connectable to the second blood passage, wherein said first and second blood pumps are adapted to move blood through the first and second blood passages in a first direction and in a reverse direction, and a pump controller operatively connected to the first and second blood pumps, said controller operates the blood pumps to cyclically move blood through the first and second blood passages in the first direction and the reverse direction.

The invention may be embodied as an extracorporeal blood processing method using a blood circuit comprising a pair of blood passages attached to opposite flow ends of a blood treatment device and said blood circuit is mounted on a blood pump console, said method comprising: withdrawing blood from a vascular system of a human patient and drawing the blood into the blood circuit; pumping the withdrawn blood through one of the pair of blood passages using a first blood pump of the console and into the blood treatment device; pumping the treated blood from the treatment device through the other of the pair of blood passages using a second blood pump of the console; infusing the treated blood from the other blood passage and into the vascular system of the patient, and periodically reversing a flow direction of blood through the pair of blood passages and blood treatment device.

Further the invention may be a method of extracorporeal blood processing method using a blood circuit comprising a pair of blood passages attached to opposite flow ends of a blood treatment device and said blood circuit is mounted on a blood pump console, said method comprising: withdrawing blood from a vascular system of a human patient and drawing the blood into the blood circuit; pumping the withdrawn blood through one of the pair of blood passages using a first blood pump of the console and into the blood treatment device; pumping the treated blood from the treatment device through the other of the pair of blood passages using a second blood pump of the console; infusing the treated blood from the other blood passage and into the vascular system of the patient; periodically reversing a flow direction of blood through the pair of blood passages and blood treatment device, and sensing a pressure in the blood passage downstream of the blood treatment device during both flow directions, and controlling a pumping rate of blood through the downstream blood passages based on the pressure in the downstream blood passage.

The invention may be further embodied as a method for monitoring a volume of filtrate in a collection bag comprising: placing the collection bag in a walled container having a displaceable surface; filtering filtrate from extracorporeal blood flowing through a blood circuit; filling the collection bag with the filtrate; as the collection bag fills with filtrate, the bag expands and displaces displaceable surface; sensing a degree of displacement of the displaceable surface, and ceasing filling the collection bag with filtrate when the degree of displacement exceeds a threshold value.

The invention may be embodied as a filtrate collection container system comprising: a container having at least one wall to receive the collection container; a displaceable wall of said container abutting the collection container; a bias applied to dispose the displaceable wall against the collection container, and a sensor detecting a force applied by the collection container against the displaceable wall.

The invention may also be embodied as a method of collecting filtrate in a filtration bag of an extracorporeal blood circuit having a blood filter, said method comprising: withdrawing blood from a mammalian patient into the blood circuit and filtering the blood with the filter; withdrawing filtrate from the filter and collecting the filtrate in an expandable container; sensing an expansion of the container as filtrate is collected in the container, and determining the container is filled with filtrate based on the expansion of the container.

The invention may be embodied as an extracorporeal blood treatment system comprising: a blood circuit comprising a first blood passage coupled at a first end to a blood filter and a second blood passage coupled at a first end to the blood filter, wherein said first and second blood passages each have a second end adapted to be coupled to a vascular system of a human patient; a first blood pump connectable to the first blood passage and a second blood pump connectable to the second blood passage, wherein said first and second blood pumps are adapted to move blood through the first and second blood passages in a first direction and in a reverse direction, and a filtrate pump withdrawing filtrate from the filter, and a pump controller operatively connected to the first and second blood pumps and to said filtrate pump.

DESCRIPTION OF PREFERRED EMBODIMENT

Figure 1:
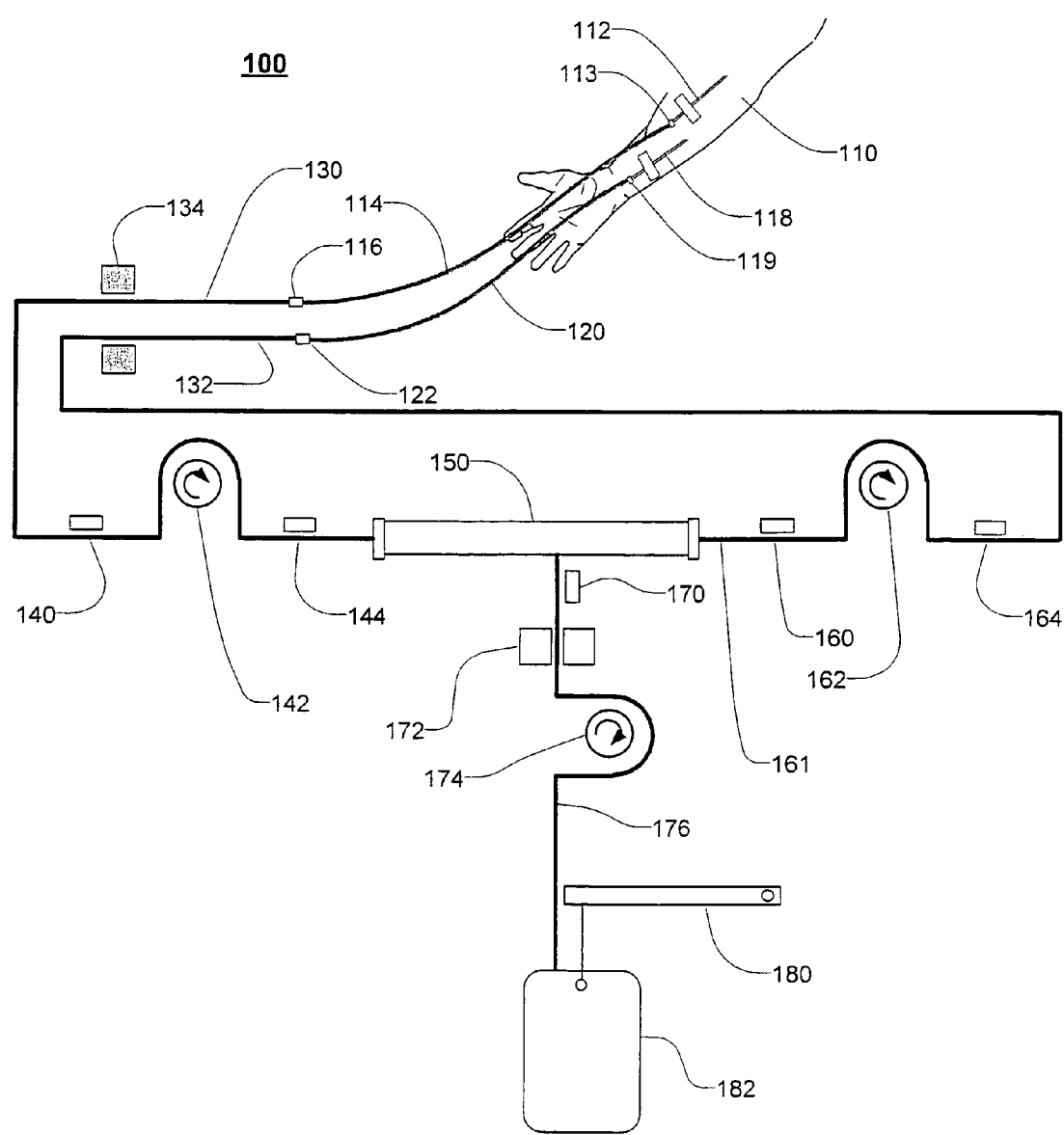
FIG. 1 is a schematic view of an ultrafiltration system.

FIG. 1 shows a schematic of the ultrafiltration system 100. Withdrawal access 112 and infusion access 118 are obtained to and from the vascular system of the patient 110. Peripheral access via standard IV access methods is acceptable for use with this device. This is an advantage of the device described herein, but not a limiting requirement. The device will function just as effectively with other higher flow access methods such as a fistula, central venous catheter, implanted port, midline or PICC.

If required, withdrawal extension 114 connects proximally to withdrawal access via connectors 113, and distally to withdrawal tubing 130 via connectors 116. If required, infusion extension 120 connects proximally to infusion access via connectors 119, and distally to infusion tubing 132 via connectors 122. If extensions 114, 120 are not required, the withdrawal tubing may connect directly to withdrawal access and infusion tubing directly to infusion access. The extensions are optional and used for making connections and extending circuit tube lines if needed. A maximum blood volume of the extension may be specified to ensure that the maximum circuit volume is within a maximum volume so that leak detection occurs without excessive loss of blood and to avoid an excessive residence time of blood in the extracorporeal circuit.

Withdrawal tubing 130 and infusion tubing 132 both pass through or in proximity of air detector 134, such that air bubbles can be detected in either tubing line. Alternatively two separate air detectors 134 may be utilized. The air detector 134 uses ultrasound to determine the presence of air. An emitter and receiver of the air detector are placed on either sides of the tubing and correctly acoustically coupled the signal transmitted between emitter and receiver and through the blood tubing. Acoustic coupling requires that a liquid be present in the tubing between the emitter and receiver. Air attenuates the signal significantly and prevents the transmission of the ultrasonic pulses thus enabling the detection of air.

Five different pressure sensors are employed in the described system 100. These are pressure sensors 140, 144, 160, 164 and 170. Pressure sensors may be of the direct contact type and part of the disposable circuit, or of the indirect contact type and part of the controlling system of the pump console. Sensors need not be the same type for each location.

After passing through the air detector, the withdrawal tubing runs through withdrawal pump 142, and then into filter 150. Infusion tubing 161 comes out the opposite end of the filter, travels through infusion pump 162, and then through the air detector. Blood traveling through the filter, is treated by extraction of liquid, with the removed filtrate media exiting the filter through the ultrafiltration line 176. Ultrafiltration media travels from the filter 150 through a blood leak sensor 172, and then ultrafiltrate pump 174. Ultrafiltration media is collected in a reservoir 182 by the ultrafiltrate pump 174 pump it though the tubing conduit 176. An optional weight scale 180 can be employed to monitor the collection of ultrafiltrate media in the reservoir. Flow rates of the infusion pump and ultrafiltrate pumps are controlled by a pump console controller so that the sum of the infusion blood flow rate and the filtrate rate equals that of the withdrawal flow rate as determined by the withdrawal pump. Pressure sensors can help monitor this flow relationship.

Pumps 142, 162, and 174 are reversible blood and filtration pumps, such as peristaltic roller pumps. The blood circuit is basically symmetrical about the filter. In particular, the length of the tubing line from the implanted port or catheter to the filter is equivalent to the length from the filter to the infusion catheter or implanted port. The first blood pump 142 is connected to a first tube line 130 of the circuit, and the second blood pump 162 is connected to the second tube line 132 of the circuit. The role of withdrawal and infusion is switched by reversing the rotational direction of the pumps. When the pumps are reversed the withdrawal access 112 is used for infusion and infusion access 118 is used for withdrawal.

Before treatment initiation, patient access is established for the vascular system. Patient access may be peripherally via standard IV needle access or via implanted blood access port(s) or other such means. To initiate treatment, the ultrafiltration circuit is primed by connecting the withdrawal connector 116 to a saline bag and the infusion connector 122 to an ultrafiltrate reservoir 182 or some other fluid collection device. The peristaltic roller pumps 142 and 162 operate in a clockwise direction until the tubing and filter are fully primed. The air detector 134 senses that the tubing and filter have no air and are fully primed. When the circuit and filter are primed, the ultrafiltration segment 176 can be primed by operating pump 174 in a clockwise direction while roller pumps 142 and 162 continue to operate in a clockwise direction. Priming of the access devices 112, 118 and extensions 114,120 can be performed through connectors 116, 122 with a syringe or other appropriate method.

Blood pumps 142 and 162 are rotated at the same speed and in the same rotational direction while ensuring that pressure 160 is positive at all times. The pressure in the tubing may fall to a negative condition due to a mismatch between pump flows that can be caused by for example the tolerances of the pump velocity settings, the tolerances of the tubing diameter and other various tubing characteristics. If the pressure sensor 160 detects a negative pressure in the blood line while pumps 142 and 162 are rotating clockwise, the controller may determine that the speed of pump 162 is to be increased or decreased to maintain the blood pressure in the circuit at a value or range of values such as 20 mmHg. The value(s) can in theory be any pressure positive or negative. Using such a closed loop control system eliminates the need for impossibly tight tolerance requirements for the pumps and tubing segments Once the circuit is primed, the patient is connected and treatment initiated. Since the blood circuit is symmetrical, pumps 142 and 162 can operate in either a clockwise or counterclockwise direction. A user specified blood flow rate will dictate how long operation can proceed in one direction before reversing. The length of time between pump reversals is calculated such that, if a disconnection occurs, the maximum amount of blood which could be pumped and lost would preferably not exceed a volume of 100 milliliters (ml), and may be set to not exceed a maximum blood loss in a range of 50 ml to 200 ml. The controller may determine the blood volume passing through the circuit based on the pump speed, and reverse the pump directions after the predetermined maximum volume, e.g., 100 ml, has passed through the circuit. After the calculated time has elapsed, pumps 142, 162 reverse direction. During clockwise rotation, the rotational rate of pump 162 is adjusted to match the rate difference of pumps 142 and 174. Thus:

$$Q \text{ pump } 142 = Q \text{ pump } 162 + Q \text{ pump } 174$$

therefore $Q$ pump $162 = Q$ pump $142 - Q$ pump $174$ where Q pump 142 is the set blood pump flow rate, Q pump 174 is the set ultrafiltrate flow rate and Q pump 162 is the difference between the set blood pump flow rate and the set ultrafiltrate flow rate.

During counterclockwise rotation, likewise the rate of pump 142 is adjusted by the controller to match the rotational rate difference of pumps 162 and 174. Thus:

$$Q \text{ pump } 162 = Q \text{ pump } 142 + Q \text{ pump } 174 \text{ therefore}$$

$$Q \text{ pump } 142 = Q \text{ pump } 162 - Q \text{ pump } 174$$

Pump 174 operates in a clockwise rotation during normal ultrafiltration mode. Ultrafiltration is controlled such that the filter removes a set fraction of fluid from the blood. The fraction is established to minimize any risk to the patient of excess blood concentration or to clot formation in the circuit. Pump 174 may operate in a counterclockwise rotation to backflush the filter or create some other desired pressure gradient across the filter. Since both infusion and withdrawal blood lines travel through the air detector 134 before reaching the patient, there is no risk of air entrainment reaching the patient from the blood circuit.

Upon reversal of direction of pumps 142 and 162, the ultrafiltration pump is temporarily stopped for a set period determined based on the set blood pump flow rate, circuit volume and access volume. During this period the pump flow rates 142 and 162 are set to equal each other because the ultrafiltrate pump 174 has been stopped. The filtrate is stopped to avoid circulating blood twice through the filter. A second pass through the filter would further concentrate the blood and could increase the propensity of clots to form in the filter. The period of filtration cessation may be determined by dividing the summation of the half the volume of the extra-corporeal circuit and the volume of blood in the access path (collectively the flush volume) by the blood pump flow rate. Since this flush volume is a function of the access methodology, the operator enters the flush volume into the ultrafiltration device at the time of setup.

Pressure sensors 140, 144, 160, 164, and 170 monitor the pressures within the circuit tubing throughout treatment to facilitate detection of disconnects or occlusions. Pressure sensors can also be used to monitor and verify pump flow rates and ultrafiltrate collection. The pressure sensor 170 is used to ensure that the filter is not exposed to excessively high TMP (Transmembrane Pressures). TMP may be calculated as:

$$TMP=((P144+P160)/2)-P170$$

Where P144 is pressure measured at pressure sensor 144, P160 is pressure measured at pressure sensor 160, and P170 is pressure measured at pressure sensor 170. Controlling the maximum negative pressure allowed at the pressure sensor site 170 ensures that the TMP does not become excessively high. The ultrafiltrate rate is limited to set ultrafiltrate rate. When the ultrafiltrate pressure 170 drops below a predefined set pressure limit, the ultrafiltrate rate is reduced to maintain the target pressure using the pressure sensor 170 as feedback. This can also be used as a trigger to backflush the ultrafiltrate to clear filter fouling. For instance when the ultratiltrate rate is less than 90% of the set ultrafiltrate rate for a 1 second period the ultrafiltrate pump 174 is reversed. During this reversal it is necessary to increase the infusion pump flow to accommodate the ultrafiltrate pump flow being returned. In the case of clockwise control this will result in the pump 162 being increased to the set flow of Q pump 142+Q pump 174.

In addition to reversing pump direction to detect disconnects and blood leaks, pump reversal can provide the benefit of clearing occlusions within the circuit and reducing the polarization layer which builds up within the filter fiber. Periodic pump reversals will reduce the chance of occlusions occurring within the circuit and access devices by flushing them every other cycle. If occlusions are detected by the pressure sensor, a pump reversal can be initiated prior to the normal cycle reversal in an attempt to resolve the cause of the occlusion. Such occlusions may occur due to vessel collapse, occlusion of cannulae tip or the formation of micro clots. Responding to them immediately will increase the probability of resolving the issue.

Figure 2:
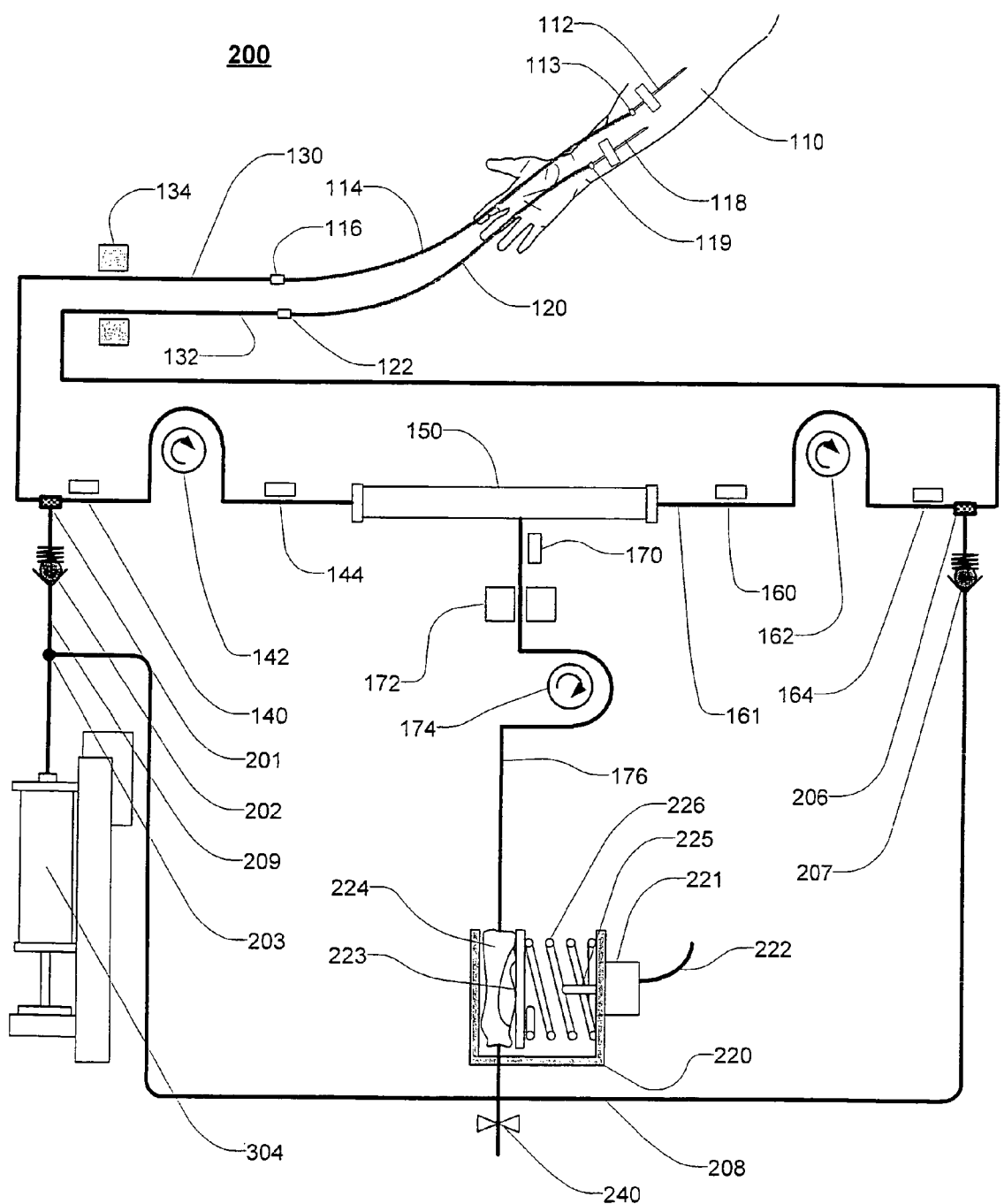
FIG. 2 is a schematic view of an ultrafiltration system with heparin infusion.

FIG. 2 is a schematic diagram of another ultrafiltration device 200 similar to the device 100 shown in FIG. 1 with the addition of an anticoagulant infusion system 203 and a position based ultrafiltrate volume limit detection system 220. Blood is withdrawn and infused through blood lines 130 and 132. The blood is withdrawn through the air detector 134 and through the filter 150 before being returned to the patient and back through the air detector 134. To prevent clotting, heparin or other such anticoagulant is infused into the withdrawal line. When blood is withdrawn from a venous supply, the blood pressure in the withdraw line will be negative and the pressure in the infusion line will be positive. By using two one way valves 202 and 207, the infused anticoagulant will always infuse into the withdrawal line obviating the need for two anticoagulant pumps or some form of motor driven actuator to switch the flow of anticoagulant when blood flow is reversed. It is generally accepted that it is better to infuse an anticoagulant upstream of the filter because the filter is in the extracorporeal circuit and has a high likelihood for initiating the clotting cascade. Infusing the anticoagulant upstream facilitates a high concentration of anticoagulant locally within the circuit and filter while minimizing systemic anticoagulation.

When blood is withdrawn by pump 142 and infused by pump 162, the pressure at the anticoagulant T connector 201 is negative and positive at T connector 206. The anticoagulation pump 304 is a syringe pump. Flows from syringe pumps are typically in the order of 0 to 20 ml/hr ranging from drug delivery flow rates of 0 to 1000 units/hr when heparin is used as the anticoagulant in hemofiltration. Since this ultrafiltration device has considerably lower blood flows, a much lower flow range of 0 to 2 ml/hr will suffice facilitating a much smaller syringe pump design. The syringe pump 304 delivers anticoagulant via the T connector 203 through two possible paths 208 or 209. When the pressure at T connector 201 is negative and T connector 206 positive the one way valve 202 is open and the one way valve 207 is closed and one way valve 207 is open ensuring the anticoagulant is delivered upstream of the filter. The T connector 203 is connected to the one way valve 202 via a conduit tube 209 and to one way valve 207 via a conduit tube 208. One way valve 203 is connected to T connector 201 via a conduit tube and one way valve 207 is connected to T connector 206 via a conduit tube. When blood flow is reversed, the polarity of the pressures at T connectors 201 and 206 will also be reversed resulting in one way valve 202 closing and one way valve 207 opening.

The ultrafiltrate removed from the filter 150 by the ultrafiltrate pump 174 is withdrawn passed the blood leak detector 172 and pumped into the collection reservoir 224 via the conduit tube 176. The blood leak detector 172 uses a near infra red (IR) photo emitter and receiver with a peak sensitivity close to the isospectic point of blood, 820 nm. In the presence of ultrafiltrate and saline little or no attenuation of the IR signal occurs but in the presence of blood the IR signal is dispersed and greatly attenuated making it possible to measure the presence of blood in ultrafiltrate. Blood in the ultrafiltrate indicates a breach of the filter membrane and when detected, causes the pumps to stop.

Because it is difficult to measure weight in an ambulatory system a volume expansion detection system is used which is independent of weight. The reservoir bag is compressed by spring 226 and plate 223. As the ultrafiltrate is delivered to the reservoir, the reservoir expands and the spring compresses. When the bag switch 221 arm 225 is intercepted by the spring plate 223 the switch is opened indicating that the bag is fully. The ultrafiltrate pump is stopped and the user is informed via an alarm that the bag has to be emptied. The bag is designed to hold 250 ml. The switch 221 is connected electrically to the system processor via cable 222. The spring creates a maximum pressure in tube 176 of 2 to 5 psi. This low maximum pressure is sufficient to compress the bag while not presenting any significant resistive force for the peristaltic pump 174. Blood circuit peristaltic pumps have been designed to relieve at pressures exceeding 60 psi. A proximity switch may also be used instead of a mechanical switch. The advantage of a mechanical switch is that it consumes no energy. The reservoir 224 may be emptied via the stopcock 240.

Ultrafiltration occurs inside the filter 150. Whole blood enters the bundle of hollow fibers from the cap of the filter canister. There are approximately 160 hollow fibers in the bundle, and each fiber is a filter. Blood flows through a channel approximately 0.2 mm in diameter in each fiber. The fiber walls of the channel are made of a porous material. The pores are permeable to water and small solutes but impermeable to red blood cells, proteins and other blood components that are larger than 50,000-60,000 Daltons. Blood flow in fibers is tangential to the surface of the filter membrane. The shear rate resulting from the blood velocity is high enough such that the pores in the membrane are protected from fouling by particles, allowing the filtrate to permeate the fiber wall. Filtrate (ultrafiltrate) leaves the fiber bundle and is collected in a space between the inner wall of the filter canister and outer walls of the fibers.

The geometry of the filter is optimized to prevent clotting and fouling of the membrane. The active area of the filter membrane is approximately 0.023 m$^2$. The permeability KUF of the membrane is 30 to 33 mL/hour/m$^2$/mmHg. These parameters allow the desired ultrafiltration rate of approximately 1 liter to 3 liters every 24 hrs at the TMP of 150 to 250 mmHg that is generated by the resistance to flow. The effective filter length is 22.5 cm and the diameter of the filter fiber bundle is 0.5 cm. The blood shear rate in the filter may be 850 to 2500 sec-1 at blood flow rate of 5 to 15 mL/min.

Since the device is to be ambulatory the return 132 and withdrawal 130 tubing may be 60 cm in length. With a tubing diameter of 2.5 mm the volume in the complete circuit blood path is less than 7 mL. With a tubing diameter of 2 mm the volume in the complete circuit blood path is less than 5 mL. Minimizing this volume reduces the blood residence time of the devices propensity to clot.

Figure 3:
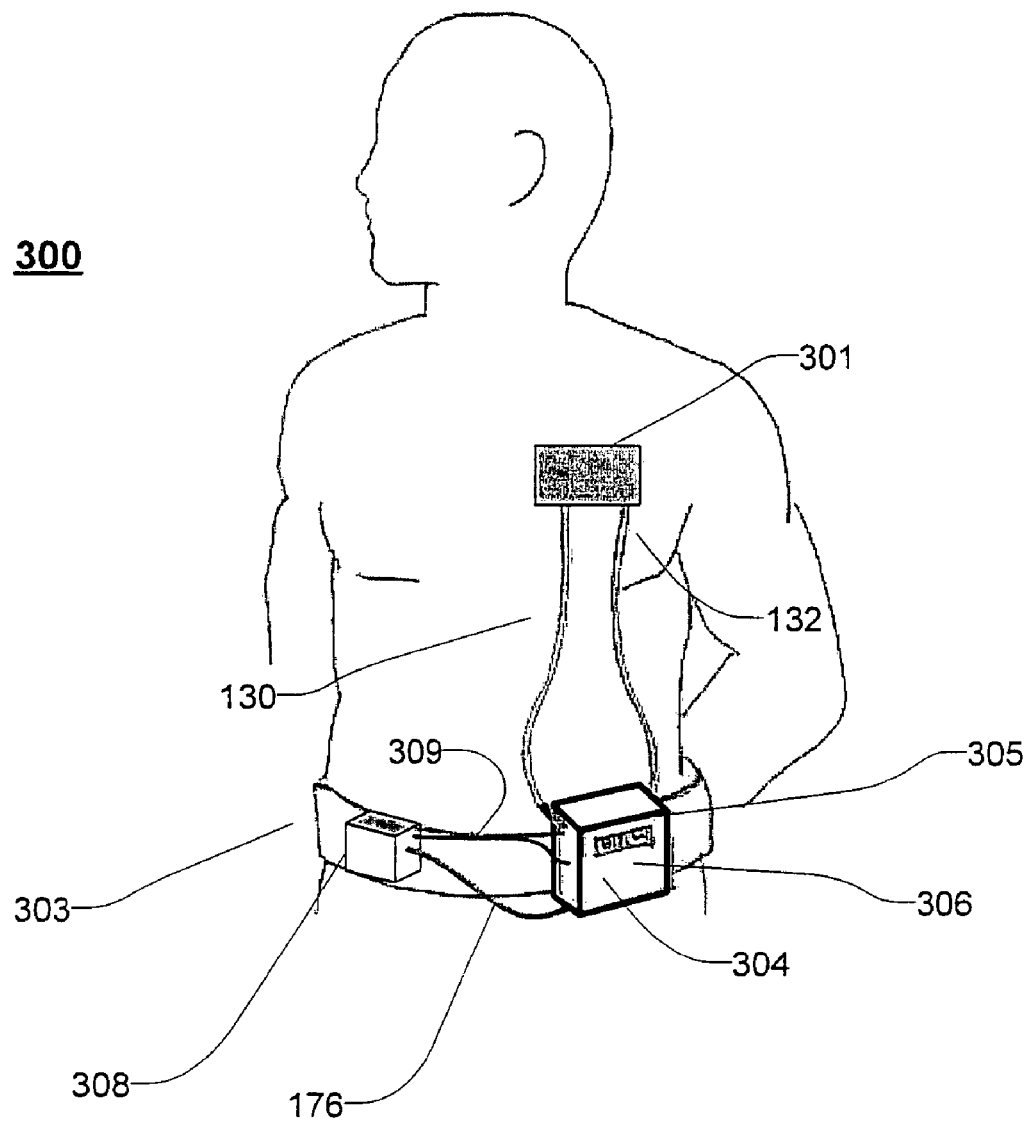
FIG. 3 illustrates of portable ultrafiltration device attached to a patient.

FIG. 3 shows a diagram of the apparatus worn by a patient as described in FIG. 2. The ultrafiltration device may be attached to a waist belt worn by the patient 300 or over the shoulder or on the back of the patient to provide ambulatory use of the device. Access to the patient blood is depicted by 301 via an implanted port with its cannulae placed centrally. Withdrawal and infusion blood lines 132 and 130 exit from the patient access site 301 and are connected to the ultrafiltration device 304 and 303 at the back of the patient. The console 304 includes a liquid crystal display (LCD) 305 and a membrane panel for viewing and entering patient therapy parameters. The reservoir 308 is separate from the console and is connected to the console via the electrical cable 309 and the ultrafiltrate conduit tube 176. Keeping the reservoir separate minimizes weight accumulation on a specific area and also reduces the hazard of wetting the console. Additional battery packs may also be stored on the belt and may be connected directly to the ultrafiltrate device as needed. When the reservoir is full the console annunciates an alarm requesting the user to empty the ultrafiltrate reservoir. A reservoir may be disconnected and emptied or drained using an extension hose connected to the reservoir minimizing the potential for spill on the patients clothing.

Figure 4:
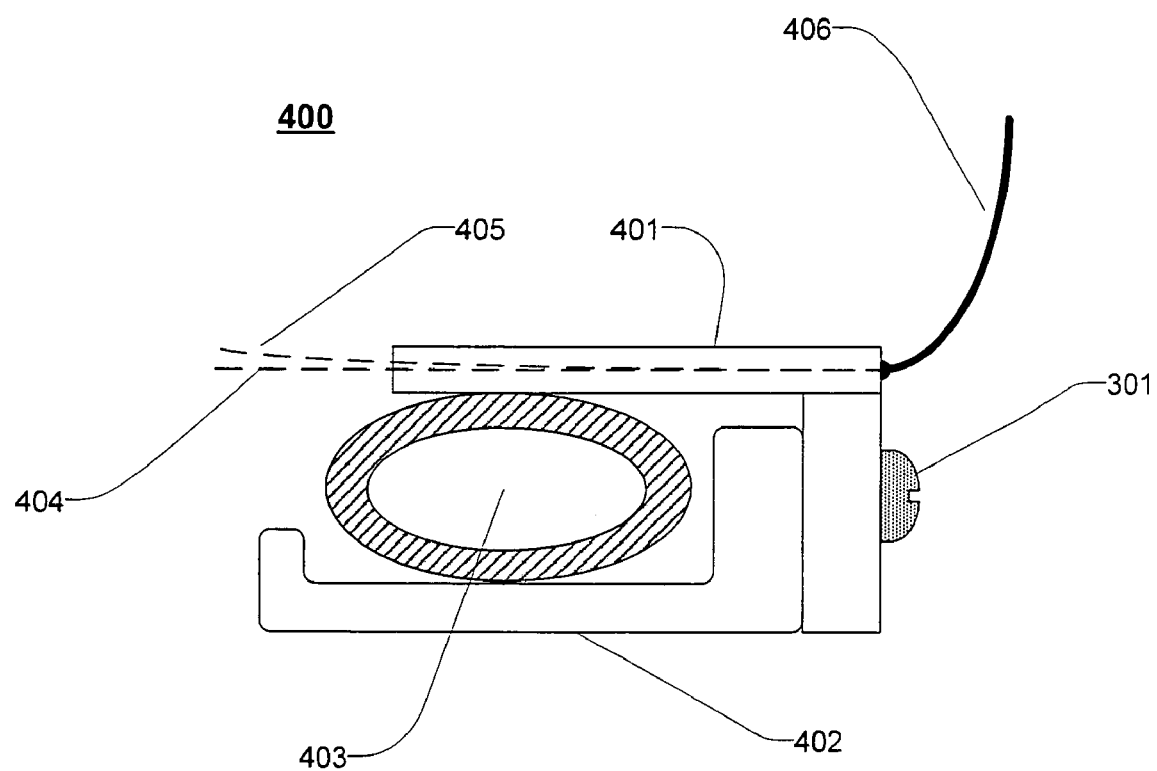
FIG. 4 is a diagram of lever arm pressure sensor.

FIG. 4 shows a detailed view of the cantilevered pressure transducer assembly 400 used for measuring pressures at sites 140, 144, 160, 164 and 172 shown in FIG. 2. The user inserts the tubing into the recess defined by the lever arm strain gauge 401 and the housing body 402. The lever arm strain gauge 401 is attached to the housing by a securing screw 301. The circuit tubing 403 which is normally cylindrical in shape is deformed to an oval shape by the insertion of the tube into the pressure transducer recess defined by 401 and 402. The lever arms 401 central axis 404 is depicted in FIG. 4 when atmospheric pressure is present within the circuit tube and when a positive pressure 405 is present within the tube. The lever arm 401 is bent upwards such that the central axis 405 when pressure is positive and bent downwards when pressure is negative. The strain gauge consists of a Wheatstone bridge resistor network on the lever arm and changes in resistance in proportion to the pressure exerted by the circuit tube. This is interpreted as an electrical signal when the transducer is excited electrically via 2 excitation wires of the 4 wire electrical cable 406.

Since the ultrafiltration device does not need pressure sensors for the detection of disconnects, a similar approach to that used to measure pressure used by standard infusion pumps may be employed. The expansion of the blood lines is used to monitor for the detection of occlusions by use of force gauges which convert the force exerted by the blood and ultrafiltrate tubing to an electrical signal. The force gauge may be a load cell similar to that sold by SMD (Strain Measurement Devices) of Meriden, Conn. and St. Edmunds, England.

The load cell may include a lever arm that applies pressure to the tubing by compressing it slightly. At the start of the treatment the measured pressure can be zeroed mathematically by the pump console microprocessor to remove offsets due to tubing position. When under positive pressure the tube expands against the load cell lever arm raising the lever arm producing an electrical signal proportional to the pressure in the tube. When under negative pressure, the tube collapses and thereby lowers the lever arm create an electrical signal proportional to the pressure in the tube. These electrical signals may be read by an analog to digital converter and translated to pressure measurements via a transfer function. Unfortunately, such pressure sensors implementations are notoriously bad for variances in offsets because of the creep characteristics of polymers. It is possible to choose polymers that minimize creep but this is a medical application and the numbers of materials that are biocompatible, have low creep properties and facilitate peristaltic action provides a significant design challenge. Peristaltic pump tubing requires that the tubing be flexible and compliant, i.e. of low durometer, otherwise the torque required to compress the tubing is excessive. It is possible to use different materials for each section of the circuit but this will create additional joints decreasing the reliability of the blood circuit. It is difficult to reliably bond different polymers materials to each other and such a construction creates an added hazard for disconnects and leaks. It is also helpful to minimize the number of transitions and joints in the circuit be minimized to decrease the circuits clotting propensity and improve circuit reliability.

Figure 5:
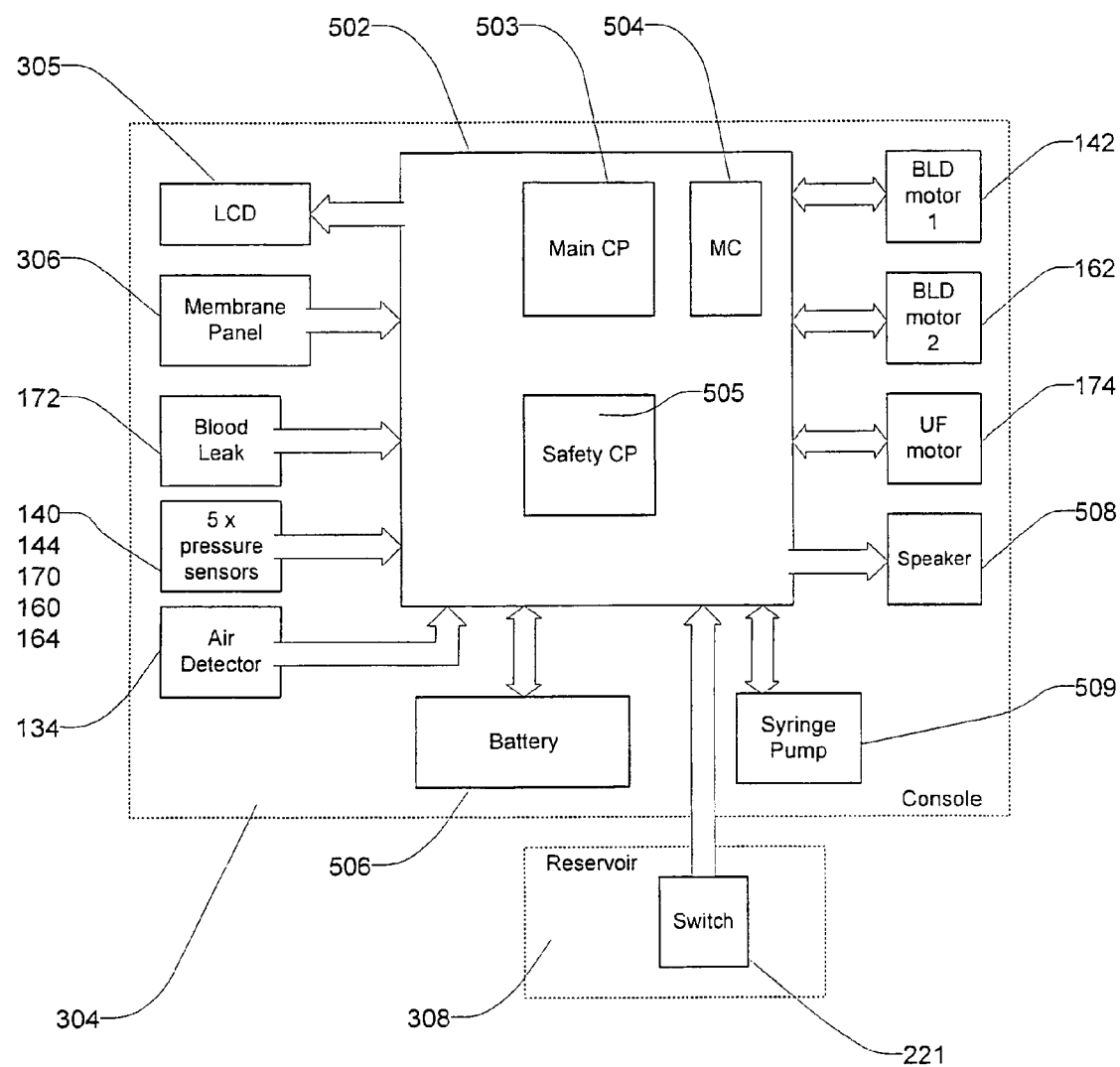
FIG. 5 is a diagram of the electrical architecture of the control system for the ultrafiltration system.

FIG. 5 shows a diagram of the electrical architecture of the ultrafiltration device consisting of the console 305 and reservoir 308. The console 304 houses the LCD 305, membrane panel 306, blood leak detector 172, pressure sensors 140, 144, 170, 160 and 164, battery pack 506, blood pumps 142 and 162, ultrafiltrate pump 174, syringe pump 508, alarm speaker 508 and main printed circuit board (PCB) 502. Within the main PC 502 there are 3 processors, the main central processor (CP) 503, the pump motor control (MC) CP 504 and the safety CP 505. Each of the sensor readings including blood leak, air detector, pump encoders and pressure sensors are shared between the main CP and the safety CP facilitating a control and monitor implementation for system safety. The pumps motors are each driven by a brushless DC motor and electrically commutated by the MC CP using encoder feedback and ½ bridge circuit on the PCB 502. Each motor has a quadrature encoder which outputs A and B quadrature digital signals as the motor is rotated as a function of motor position.

Each motor is geared for optimal efficiency with a gear ratio of 10:1 resulting in a peak power consumption of less than 2 watts per motor. In order to conserve energy the pressure sensors, blood leak detector and air detector are only powered when it is necessary to read the sensor signal. This reduces the power consumption of these devices by a factor of 10. The digital sample rate for the console sensors is 50 Hz. The console battery pack operates at 12 VDC and uses NiMH chemistry. Charging of the batteries is performed off line with a separate battery charger. This reduces the electrical circuitry required during operation and minimizes power consumption and space requirements. Use of an external power source is possible via and external power supply with an output of 12 VDC. The battery supply is disabled when an external power supply is connected.

The reservoir 308 is connected electrically via a 2 wire cable to the console 304 providing electrical connection for the reservoirs expansion limit mechanical switch 221. The mechanical switch 221 is normally closed until the reservoir is full. When full the switch is thrown open providing the additional safety that if the electrical cable were to become disconnected ultrafiltration would be stopped.

The main CP reads each of the pressure inputs and updates the blood and ultrafiltrate pumps velocity every 20 ms. The liquid crystal display (LCD) is only powered if it has a message to display or if the operator presses a membrane panel key. The console duty cycles a green light emitting diode (LED) every second to indicate that it is operating correctly. In the event of a problem, a red LED is flashed and an alarm annunciated via the speaker. The LCD is then powered on and displays a message informing the users of the potential cause of the issue and remedy.

Figure 6:
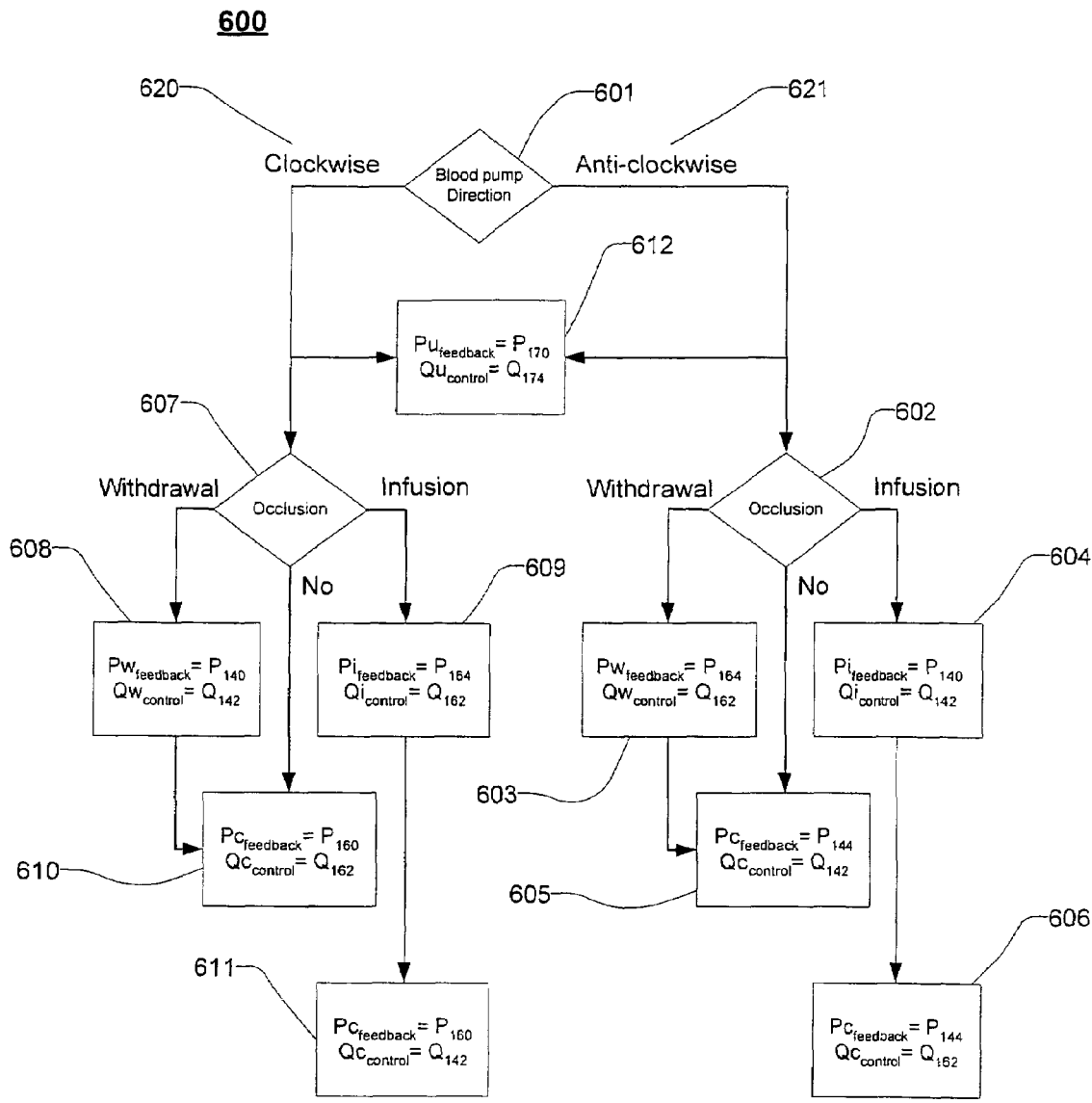
FIG. 6 is a flow chart of the pressure control algorithm including feedback sensors and actuators under various occlusion conditions.

FIG. 6 shows a flow chart of which pressure sensors the ultrafiltration device uses for feedback when in clockwise or anticlockwise blood pump rotation and which pumps it uses to control these pressures to limit pressure excursions. Four pressure control loops are operating simultaneously. These loops are: (i) the withdrawal pressure control algorithm, (ii) the infusion pressure control algorithm, (iii) the filter positive pressure control algorithm and (iv) the ultrafiltrate pressure control algorithm In flow chart 600 the terms Pxfeedback and Qxcontrol are used where P denotes pressure, Q flow of pump, x the control algorithm i.e. w withdrawal, i infusion, c filter pressure or center pressure and u ultrafiltrate.

During blood pump reversals of pumps 142 and 162 from anti-clockwise rotation to clockwise rotation the pressure transducers used for feedback are changed in conjunction with the blood pumps used for control. During clock wise rotation 620, the pressures within the filter are kept slightly positive by using the pressure sensor 160 as feedback and the blood pump 162 as control as shown in block 610. This is also true in the event of a withdrawal occlusion because the pressure sensor 140 is used as feedback and the blood pump 142 is used as the control blood pump as shown in block 608. No conflict arises between two control loops trying to control the same pressure. But in the case of an infusion occlusion when the blood pumps are rotating clockwise the pressure sensor 164 is used as feedback and the blood pump 162 is used as control as shown in block 609.

To maintain positive pressure within the filter the same feedback pressure sensor 160 is used as shown in blocks 610 and 611 but the control pump is changed from 162 to 142. This eliminates any conflict between which pump is used for control while still maintaining both pressure targets. The withdrawal and infusion pressure targets read by pressure sensors 140 and 160 respectively are −300 and 300 mmHg respectively. The blood pump flows are limited by the user defined set blood pump flow which is set to be as high as possible based upon the available access minimizing blood circuit residence time and maximizing the maximum rates of ultrafiltration. The maximum extraction rate of ultrafiltrate is limited to 21% of blood flow. If an infusion occlusion is persistent for an extended period of time then the direction of the blood pumps are reversed. Blood pump reversals are normally timed based and are a function of set blood pump flow but in the vent of a persistent occlusion in either the withdrawal or infusion line the reversal sequence may be initiated early.

During blood pump reversals of pumps 142 and 162 from clockwise rotation to anticlockwise rotation the pressure transducers used for feedback are changed in conjunction with the blood pumps used for control. During anticlockwise rotation 621 the pressures within the filter are kept slightly positive by using the pressure sensor 144 as feedback and the blood pump 142 as control as shown in block 605. This is also true in the event of a withdrawal occlusion because the pressure sensor 164 is used as feedback and blood pump the blood pump 162 is used as the control blood pump as shown in block 608. No conflict arises between two control loops trying to control the same pressure. But in the case of an infusion occlusion when the blood pumps are rotating anticlockwise the pressure sensor 140 is used as feedback and the blood pump 142 is used as control as shown in block 604. In order to maintain positive pressure within the filter the same feedback pressure sensor 144 is used as shown in blocks 605 and 606 but the control pump is changed from 142 to 162. This eliminates any conflict between which pump is used for control while still maintaining both pressure targets.

During both clockwise and anticlockwise blood pump rotation the ultrafiltrate pressure is limited to a maximum negative pressure of −300 mmHg., for example. Block 612 shows that the pressure sensor 174 and ultrafiltrate pump 174 are unaffected by blood pump direction.

Figure 7:
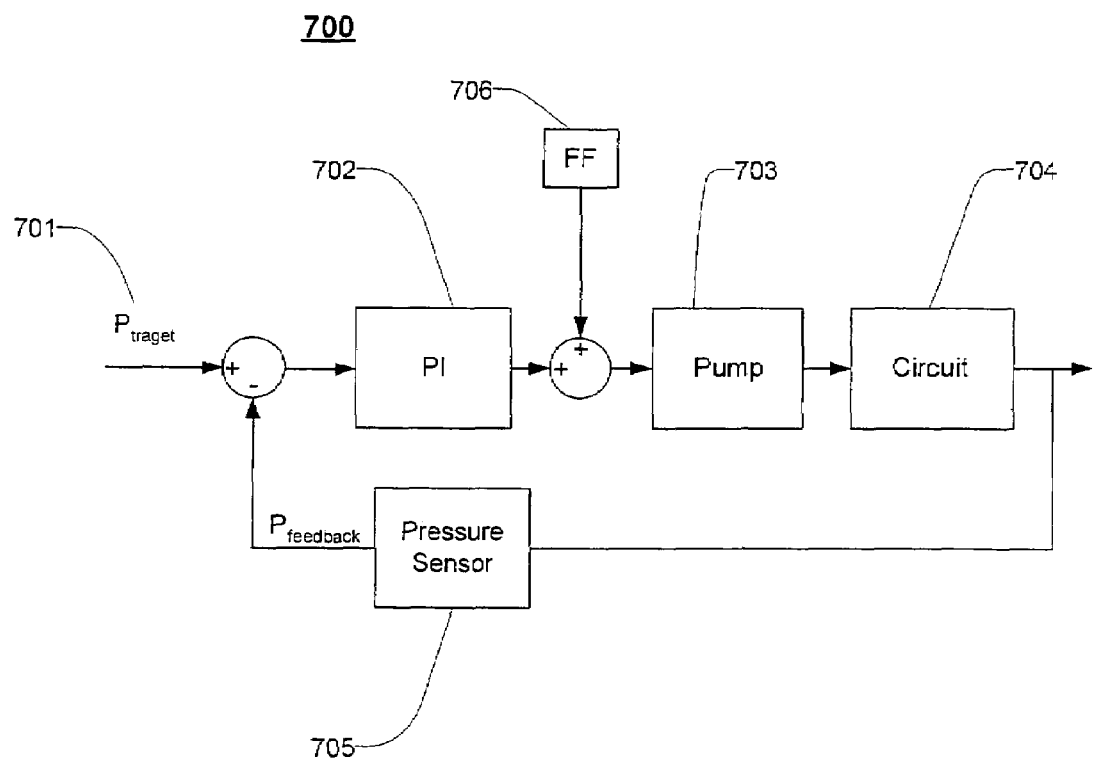
FIG. 7 is a flow chart of the Proportional Integral (PI) pressure control algorithm.

FIG. 7 shows how the pressure control loop 700 is implemented. This pressure control loop is used for all four control loop described in FIG. 6. The difference between the target pressure 700 and the feedback pressure 705, the pressure error are input to a PI (Proportional Integral) control loop 703. Each time there is a setting change to the blood flow, UF rate or the ultrafiltrate pump has to be reversed as part of a back flush maneuver the feed forward term (FF) 706 is updated to difference between the set blood flow and the UF rate. Thus in the case of clockwise control the FF term 706 is set to:

$$FF = Q \text{ pump } 162 = Q \text{ pump } 142 - Q \text{ pump } 174$$

Upon initiation of the control loop the integration term of the PI loop is set to 0 ml and is limited to +/−20% of the set blood flow rate to prevent windup of the integrator. Thus if the blood flow is set to 10 ml/min the maximum the integration term if allowed to sum to is +/−1 ml/min when trying to the pressure sensor 160 to the target pressure $P_{target}$. The +/−20% limit is chosen because the blood pump has an accuracy of +/−10% and variations significantly above of below this imply a fault condition.

The resultant pump flow of the summed PI output and the FF term is commanded by the MC CP to the pump 703 which delivers the desired fluid flow and results in a circuit 704 causing the pressure 705 due to the circuit and access resistance. This pressure 705 is read by the Main CP using an ADC (Analog to Digital Convertor) and is used to calculate the pressure error by subtracting the feedback pressure 705 from the target pressure 701.

FIGS. 8a to 8k are diagrams depicting the air detector and cross-sections of the withdrawal and return tube passing through the air detector. The dual lumen tube design eliminates the need for a second air detector and also reduces the power consumption requirements for the device. This minimizes the required space, weight and battery capacity for device operation.

The air detector 801 uses an ultrasonic emitter 802 and receiver 803. The withdrawal 802 and return tube 804 are inserted into the air detector slot and as long as the lumens are full of liquid no air detection will be detected. If a bubble of gas is entrained into the withdrawal of return tube, passes through the air detector and is greater than 50 microliters in volume, an air detected alarm is annunciated by the console. The signal strength received by the receiver will dramatically reduce in the presence of an air bubble because a gas is significantly less dense than a liquid and there are large losses in the energy being transmitted making the detection of bubbles possible. This will be interpreted as an air detected alarm by the ultrafiltration device. Testing has shown that it is possible to insert two single circular single lumen tubes into a standard air detector and to detector air in either lumen. It is difficult to place such single lumens into the air detector slot and a better alternative is to extrude the two lumens together. FIGS. 8b to 8k show the many combinations of tubing cross-section supporting dual, triple and multiple lumens which will support such an air detection implementation. The patient circuit tubing is inserted into the air detector slot during the priming sequence of the ultrafiltration device.

Figure 8A:
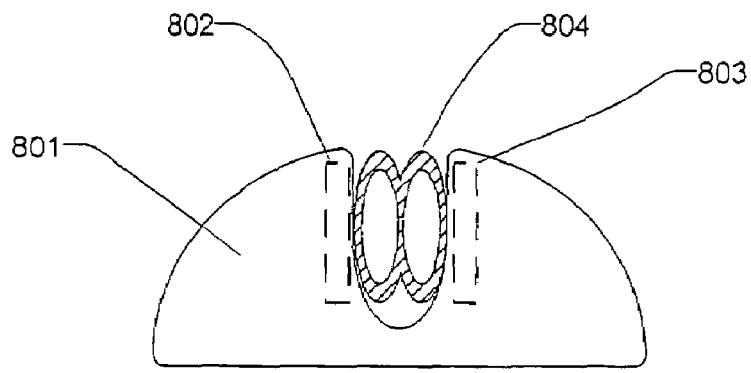
FIGS. 8a to 8k show diagrams of the air detector and tubing configuration.
Figure 8B:
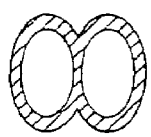
Figure 8C:
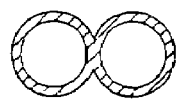
Figure 8D:
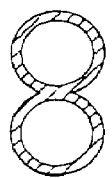
Figure 8E:
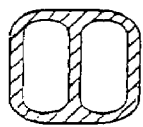
Figure 8F:
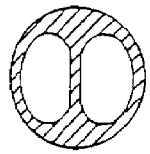
Figure 8G:
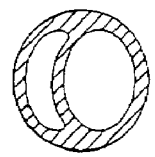
Figure 8H:
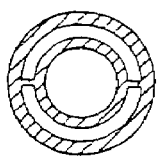
Figure 8I:
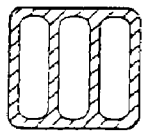
Figure 8J:
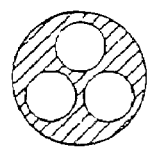
Figure 8K:
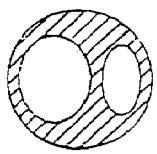

FIG. 8b shows a dual oval shaped co-extruded cross-section. It would also possible to make such a portion of tubing by gluing two tubes together to facilitate. FIGS. 8c and 8d show an hour glass dual circular co-extruded cross-section in both the horizontal and vertical position demonstrating orientation is not important when inserting the tubing segment into the air detector for the purposes of detecting air. Such a cross-section could be extruded or be formed from gluing two tubes together as part of the circuit manufacturing process. Either extruding or gluing will enable a similar cross-section. The cross-section of the two lumen tubing is also not limited to being hour glass shaped, it may be square in shape as shown in FIG. 8e or circular with two inner D lumen as shown in FIG. 8f or a combination of two lumen shapes ranging from circular and oval to kidney shaped as shown in FIG. 8g. FIG. 8h shows a co-extruded concentric tubing cross-section which will also work. Air in either channel will result in an air detection alarm. FIG. 8k shows a double oval lumen implementation of a dual lumen tubing implementation. The purpose of showing these configurations is to demonstrate that the implementation is not limited to a specific tubular configuration and that many implementations are feasible.

This air detection scheme will also work for multiple lumens. FIG. 8i shows a three lumen implementation using a square profile. FIG. 8j shows a similar three lumen implementation using a circular lumen profile. The detection method will work with multiple lumens as shown in FIGS. 8b to 8k.

The invention has been described in connection with what is presently considered to be the most practical and preferred embodiments. The invention is not to be limited to the disclosed embodiments, but, on the contrary, covers various modifications and equivalent arrangements included within the spirit and scope of the appended claims.

What is claimed is:

1. An extracorporeal blood treatment system comprising:
  a blood circuit comprising a first blood passage coupled to a blood treatment device coupled to a first end of the treatment device and a second blood passage coupled to an opposite end of the treatment device, wherein said first and second blood passages are each adapted to be coupled to a vascular system of a human patient;
  a reversible first blood pump connectable to the first blood passage and a reversible second blood pump connectable to the second blood passage, wherein said first and second blood pumps are adapted to reverse pumping directions to move blood through the first and second blood passages in a first direction and alternatively in a reverse direction, wherein blood is withdrawn from a patient into the first blood passage and infused into the patient through the second blood passage while the first and second blood pumps turn in a first direction, and blood is withdrawn from the patient into the second blood passage and infused into the patient through the first blood passage while the first and second blood pumps turn in an opposite direction, and
  a pump controller operatively connected to the first and second blood pumps, said controller operates the blood pumps to reverse the pumping directions to cyclically move blood through the first and second blood passages in the first direction and in the reverse direction a filter having a filtrate output tube and said system further comprises a filtrate pump connectable to the filtrate output tube, wherein the filtrate pump is temporarily stopped while the blood flow though the circuit is reversed.

2. The extracorporeal blood treatment system in claim 1 wherein the blood treatment device is a blood filter.

3. The extracorporeal blood treatment system in claim 1 wherein the blood treatment device is an ultrafiltration blood filter.

4. The extracorporeal blood treatment system in claim 1 wherein said pump controller cyclically switches the blood pumps to reverse the blood direction after a volume of blood pumped through the first blood passage is between 50 ml and 200 ml.

5. The extracorporeal blood treatment system in claim 1 wherein said pump controller cyclically switches the blood pumps to reverse the blood direction after a flow volume of blood pumped through the second blood passage is between 50 milliliters (ml) and 200 ml.

6. The extracorporeal blood treatment system in claim 1 wherein the first blood passage and second blood passage each include a tube connectable to a catheter.

7. The extracorporeal blood treatment system in claim 1 wherein the first blood passage and second blood passage each include a tube connectable to an implanted blood access device.

8. The extracorporeal blood treatment system in claim 1 wherein said controller operates the blood pumps to move blood through the circuit at a flow rate in a range of five milliliters per minute (ml/min) to fifteen ml/min.

9. The extracorporeal blood treatment system in claim 1 further comprising a first air in blood detection device coupled to the first blood passage and a second air in blood detection device coupled to the second blood passage.

10. The extracorporeal blood treatment system in claim 1 further comprising blood pressure sensors coupled to each of the first and second blood pumps.

11. An extracorporeal blood treatment system comprising:
  a blood circuit comprising a first blood passage coupled to a blood treatment device coupled to a first end of the treatment device and a second blood passage coupled to an opposite end of the treatment device, wherein said first and second blood passages are each adapted to be coupled to a vascular system of a human patient;

a reversible first blood pump connectable to the first blood passage and a reversible second blood pump connectable to the second blood passage, wherein said first and second blood pumps are adapted to reverse pumping directions to move blood through the first and second blood passages in a first direction and alternatively in a reverse direction, wherein blood is withdrawn from a patient into the first blood passage and infused into the patient through the second blood passage while the first and second blood pumps turn in a first direction, and blood is withdrawn from the patient into the second blood passage and infused into the patient through the first blood passage while the first and second blood pumps turn in an opposite direction, and a pump controller operatively connected to the first and second blood pumps, said controller operates the blood pumps to reverse the pumping directions to cyclically move blood through the first and second blood passages in the first direction and in the reverse direction, wherein the first and second blood pumps are operated simultaneously.

12. An extracorporeal blood treatment system comprising:

a blood circuit comprising a first blood passage coupled to a blood treatment device coupled to a first end of the treatment device and a second blood passage coupled to an opposite end of the treatment device, wherein said first and second blood passages are each adapted to be coupled to a vascular system of a human patient;

a reversible first blood pump connectable to the first blood passage and a reversible second blood pump connectable to the second blood passage, wherein said first and second blood pumps are adapted to reverse pumping directions to move blood through the first and second blood passages in a first direction and alternatively in a reverse direction, wherein blood is withdrawn from a patient into the first blood passage and infused into the patient through the second blood passage while the first and second blood pumps turn in a first direction, and blood is withdrawn from the patient into the second blood passage and infused into the patient through the first blood passage while the first and second blood pumps turn in an opposite direction;

a pump controller operatively connected to the first and second blood pumps, said controller operates the blood pumps to reverse the pumping directions to cyclically move blood through the first and second blood passages in the first direction and in the reverse direction, and a filter having a filtrate output tube and said system further comprises a filtrate pump connectable to the filtrate output tube, wherein said pump controller further stops the filtrate pump until a specific blood volume is displaced by the blood pumps after the blood pumps reverse direction.

* * * * *